(12) United States Patent
Clement

(10) Patent No.: US 10,842,679 B2
(45) Date of Patent: Nov. 24, 2020

(54) BODY CAST FOR THE HUMAN BODY

(71) Applicant: The Buddyguard Corporation, Northridge, CA (US)

(72) Inventor: Margarita Clement, Northridge, CA (US)

( * ) Notice: Subject to any disclaimer, the term of this patent is extended or adjusted under 35 U.S.C. 154(b) by 0 days.

(21) Appl. No.: 16/792,727

(22) Filed: Feb. 17, 2020

(65) Prior Publication Data

US 2020/0179175 A1 Jun. 11, 2020

Related U.S. Application Data

(63) Continuation of application No. 15/642,326, filed on Jul. 5, 2017, now Pat. No. 10,568,774.

(60) Provisional application No. 62/358,282, filed on Jul. 5, 2016.

(51) Int. Cl.
| | |
|---|---|
| *A61F 13/04* | (2006.01) |
| *A61F 13/00* | (2006.01) |
| *A61F 5/058* | (2006.01) |
| *A61F 5/30* | (2006.01) |

(52) U.S. Cl.
CPC .......... *A61F 13/041* (2013.01); *A61F 5/0585* (2013.01); *A61F 5/05825* (2013.01); *A61F 5/30* (2013.01); *A61F 2013/00489* (2013.01); *A61F 2013/00578* (2013.01); *A61F 2013/00604* (2013.01); *A61F 2013/00625* (2013.01); *A61F 2013/00634* (2013.01); *A61F 2013/00974* (2013.01)

(58) Field of Classification Search
CPC .. A61F 13/041; A61F 5/05825; A61F 5/0585; A61F 5/30; A61F 2013/00489; A61F 2013/00578; A61F 2013/00604; A61F 2013/00625; A61F 2013/00974; A61F 5/01; A61F 5/058; A61F 5/0102; A61F 2013/00634
See application file for complete search history.

(56) References Cited

U.S. PATENT DOCUMENTS

| | | | |
|---|---|---|---|
| 2007/0027419 A1* | 2/2007 | Drennan | A63B 21/4011 602/19 |
| 2016/0113801 A1* | 4/2016 | Weissleder | A61F 5/0104 602/19 |

* cited by examiner

*Primary Examiner* — Ophelia A Hawthorne
(74) *Attorney, Agent, or Firm* — Aslan Law, P.C.

(57) ABSTRACT

An apparatus comprising a support wrap. The support wrap including at least an upper portion, the upper portion of said the support wrap having a first side extending along a first direction by a first length, the upper portion of said the support wrap having a second side extending along a second direction by a second length, the upper portion of said the support wrap having a third side extending along a third direction by a third length, the first direction is in a different direction than the second direction, the first direction is in a different direction than the third direction, the first length being greater than the second length, the first length being greater than the third length, the upper portion including a first upper fastening member, and said first upper fastening member capable of fastening said first side to said second side.

15 Claims, 8 Drawing Sheets

FIG. 3

BODY CAST FOR THE HUMAN BODY

CROSS REFERENCE OF RELATED APPLICATIONS

This application is a Continuation Application of and claims the benefit of priority to U.S. patent application Ser. No. 15/642,326 filed on Jul. 5, 2017, U.S. patent application Ser. No. 15/642,326 claims the benefits of U.S. provisional application No. 62/358,282, filed Jul. 5, 2016 and entitled LABEL PROTECTIVE CLOSURE FOR BODY CAST AND ACCESSING PATIENT INFORMATION, which the entire contents of provisional application and the entire contents of U.S. patent application Ser. No. 15/642,326 are incorporated by reference herein in their entirety.

FIELD OF THE INVENTION

The present invention relates generally to a system and method for donning and labeling a body cast enables a body cast to be donned and labeled, so as to provide support and protection for the body and enable access to patient information directly from the body cast. More so, a system and method for donning and labeling a body cast provides a protective body cast that forms padded protection around the lower torso and legs of a bedridden patient; and especially around the hip, buttock, and lower extremity pressure points; whereby the body cast includes a multi-layered enclosing cloth support wrap that is fabricated from a nanomaterial, an inner surface having padding, and at least one auxiliary padding that detachably attaches to the body cast for additional padding; whereby at least one label detachably attaches to the lower portion of the support wrap for indicating information pertinent to the patient; and whereby the label is easily accessible to a caregiver for reading and marking directly on the bedridden patient.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Typically, a body cast is used to immobilize the hips and thighs of a patient to assist in the healing of bones, muscles and tendons. Body casts are typically used on children following surgery or a reduction to hold the hips in a position that facilitates bone growth. The casts may begin at the chest and extend to cover both legs down to the toes or knee, or one leg down to the toes or knee and the other leg down to the hip or knee. A similar type of cast known as an abduction boot extends from the upper thigh of each leg down to the foot.

Often, medical patient recordkeeping systems usually involve charts containing information relating to the treatment of the patient and personal identification systems such as medical patient wristbands worn by the medical patient to correlate the patient, the patient's records, and the patient's treatment. Providers of medical services have a strong interest in maintaining accurate medical patient information in the most efficient manner possible.

It is known in the art of medical patient recordkeeping to make printed adhesive labels for affixation to a medical patient's medical charts. It is further well known to print wristbands for medical patients to wear for identification. The making of such chart and wristband labels has historically been done by hand. With the advent of computers, the making of chart labels became easier, especially where such chart labels could be printed on a single sheet of adhesive label paper on a computer printer.

Other proposals have involved protecting the body with a cast and labeling a medical patient. The problem with these systems is that they do not provide both functions simultaneously. Even though the above cited body cast and medical labeling systems meets some of the needs of the market, a system and method for donning and labeling a body cast to enable facilitated donning and informative labeling of a body cast; and whereby the body cast is easily labeled with patient information, so as to provide the dual purpose of supporting the body and accessing patient information directly on the body of the patient, is still desired.

SUMMARY

Illustrative embodiments of the disclosure are generally directed to a system and method for donning and labeling a body cast. The system and method is configured to enable facilitated donning and informative labeling of a body cast. The body cast is easily labeled with patient information, so as to provide the dual purpose of supporting the body and accessing patient information directly on the body of the patient.

The system and method provides a support wrap with an upper portion, wherein the upper portion of said the support wrap having a first side extending along a first direction by a first length, the upper portion of said the support wrap having a second side extending along a second direction by a second length, the upper portion of said the support wrap having a third side extending along a third direction by a third length, the first direction is in a different direction than the second direction, the first direction is in a different direction than the third direction, the first length being greater than the second length, the first length being greater than the third length, the upper portion including a first upper fastening member, said first upper fastening member capable of fastening said second side to said third side, and the upper portion of said the support wrap having a fourth side extending along a fourth direction by a fourth length; a first lower portion; and a second lower portion, wherein the first lower portion extending from the fourth side and extending away from upper portion, and the second lower portion extending from the fourth side and extending away from upper portion.

In at least one embodiment, said first upper fastening member includes a first hook and loop mechanism extending along the first direction.

In at least one embodiment, said first upper fastening member includes a first hook and loop mechanism extending along the first direction, and said first hook and loop mechanism creates a handle in a case that the first hook and loop mechanism is fastened.

In at least one embodiment, said first upper fastening member includes a first hook and loop mechanism extending along the first direction, and a second upper fastening member includes a second hook and loop mechanism extending along the first direction.

In at least one embodiment, a second upper fastening member includes a first hook and loop mechanism extending along the first direction, and a third upper fastening member includes a second hook and loop mechanism extending along the first direction.

In at least one embodiment, the first lower portion includes at least a first lower fastening member.

In at least one embodiment, the first lower portion includes at least a first lower fastening member, and the second lower portion includes at least a second lower fastening member.

In at least one embodiment, the first lower portion includes at least a first lower fastening member, the second lower portion includes at least a second lower fastening member, the first lower fastening member includes a first hook and loop mechanism, and the second lower fastening member includes a second hook and loop mechanism.

In at least one embodiment, the upper portion having an inner surface and an outer surface, and the outer surface including the first upper fastening member.

In at least one embodiment, the first lower portion includes a first lower fastening member, and the first lower portion includes a second lower fastening member.

In at least one embodiment, the first lower portion includes a first lower fastening member, the first lower portion includes a second lower fastening member, the first lower fastening member includes a first hook and loop mechanism, and the second lower fastening member includes a second hook and loop mechanism.

In at least one embodiment, the area of said first side is different from the area of said second side.

The system and method provides a support wrap with an upper portion, wherein the upper portion of said the support wrap having a first side extending along a first direction by a first length, the upper portion of said the support wrap having a second side extending along a second direction by a second length, the upper portion of said the support wrap having a third side extending along a third direction by a third length, the first direction is in a different direction than the second direction, the first direction is in a different direction than the third direction, the first length being greater than the second length, the first length being greater than the third length, the upper portion having an inner surface and an outer surface, the outer surface including a first upper fastening member, said first upper fastening member capable of fastening said second side to said third side, and the upper portion of said the support wrap having a fourth side extending along a fourth direction by a fourth length; a first lower portion; a second lower portion; a first transition portion; a second transition portion; the first transition portion extending from the fourth side and extending away from upper portion, the first transition portion having a first transition width, the second transition portion extending from the fourth side and extending away from upper portion, the second transition portion having a second transition width, the first lower portion extending from the first transition portion and extending away from upper portion, the first lower portion having a first lower width, the second lower portion extending from the first transition portion and extending away from upper portion, the second lower portion having a second lower width, the first lower width and the second lower width are greater than the first transition width and the second transition width, and the first length and the fourth length are greater than the first transition width, the second transition width, the first lower width and the second lower width.

In at least one embodiment, the first lower portion includes at least a first lower fastening member.

In at least one embodiment, the first lower portion includes at least a first lower fastening member, and the second lower portion includes at least a second lower fastening member.

In at least one embodiment, the first lower portion includes at least a first lower fastening member, the second lower portion includes at least a second lower fastening member, the first lower fastening member includes a first hook and loop mechanism, and the second lower fastening member includes a second hook and loop mechanism.

In at least one embodiment, the upper portion having an inner surface and an outer surface, and the outer surface including the first upper fastening member.

In at least one embodiment, the first lower portion includes a first lower fastening member, and the first lower portion includes a second lower fastening member.

In at least one embodiment, the first lower portion includes a first lower fastening member, the first lower portion includes a second lower fastening member, the first lower fastening member includes a first hook and loop mechanism, and the second lower fastening member includes a second hook and loop mechanism.

In at least one embodiment, the area of said first side is different from the area of said second side.

The system and method provides a protective body cast that forms padded protection around the body of a bedridden patient. The body cast may enclose the lower torso and legs; and especially the hip, buttock, and lower extremity pressure points of the body. In one possible embodiment, the body cast consists of a nanomaterial, essentially serving as an envelope for an inner lining of a softer material such as a composite foam rubber.

In another embodiment, the body cast is sectioned into a multi-layered enclosing cloth support wrap that is fabricated from a nanomaterial, an inner surface having padding, and at least one auxiliary padding that detachably attaches to the body cast for additional padding. At least one label detachably attaches to the lower portion of the support wrap. The label is configured to help indicate personal and medical information that is pertinent to the patient. In this manner, a caregiver may easily read and mark directly on the bedridden patient.

In one embodiment, the system and method for donning and labeling a body cast to provide cushioning for a patient's body from waist to knee and access patient information, comprises:
  a body cast including:
    a cloth support wrap defined by a nanomaterial, the nanomaterial including at least one of the following: nylon, rayon and Dacron,
    the cloth support wrap comprising an upper portion defined by a plurality of upper free ends, the upper portion operable to at least partially enclose a lower torso when the plurality of upper free ends overlap, the upper portion of the support wrap further being defined by a crotch region,
    the cloth support wrap further comprising a pair of lower portions defined by a plurality of lower free ends, the pair of lower portions operable to enclose a leg when the plurality of lower free ends overlap;
    an inner lining defined by a pliable foam rubber material, the inner lining being coplanar to the support wrap, whereby the inner lining helps cushion the lower torso and the legs;

at least one auxiliary padding detachably attachable to the body cast, whereby the at least one auxiliary padding helps provide cushioning for the lower torso and the legs;

a plurality of fasteners placed at predetermined locations on the support wrap, the plurality of fasteners enabling closure of the cloth support wrap around the lower torso and the legs; and at least one label defined by a field, the field being sized and dimensioned to enable marking information, the at least one label detachably attachable to the upper portion, or the pair of lower portions, or both of the support wrap.

In another aspect, the enclosing support wrap is fabricated of a low friction material.

In yet another aspect, the nanomaterial is selected from the group consisting of nylon, rayon and Dacron.

In yet another aspect, the nanomaterial comprises nanominerals infused and crystalized into the nanomaterial.

In yet another aspect, the nanomaterial is water resistant, dirt free, odorless, anti-UV, and antibacterial.

In yet another aspect, the plurality of fasteners are a plurality of hook and loop latches, each hook and loop latch having a hook tape and a loop tape of a predetermined size.

In yet another aspect, the loop tape is larger than the hook tape to permit adjustment of the size of the body cast, when it is wrapped around a patient's body.

In yet another aspect, the upper portion of the support wrap comprises a crotch region that is sized to enable facilitated catherization and urination to the crotch.

In another aspect, the at least one label is a card.

In another aspect, the at least one label is configured to adhere to the pair of lower portions with an adhesive, a pin, or a hook and loop fastener.

In another aspect, the at least one label is disposed on the pair of lower portions, such that the patient does not have to be turned over to read and mark the at least one label.

In another aspect, the at least one label comprises a plurality of fields for marking information pertinent to the patient, whereby the information includes at least one member selected from the group consisting of: a name of the bedridden patient, a time the patient was last examined, and instructions from a caregiver.

One objective of the present invention is to envelop the lower torso and legs in a protective body cast.

Another objective is to manufacture the body cast from a low friction nanomaterial to enhance donning and comfort thereof.

Yet another objective is to provide various fasteners to secure the body cast to the lower torso and legs.

Yet another objective is to provide an auxiliary padding to the cast to cushion the lower torso and legs.

Yet another objective is to provide at least one label that detachably attaches to the body cast for reading information about a bedridden patient.

Yet another objective is to provide an inexpensive to manufacture body cast,

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

Figure 3:
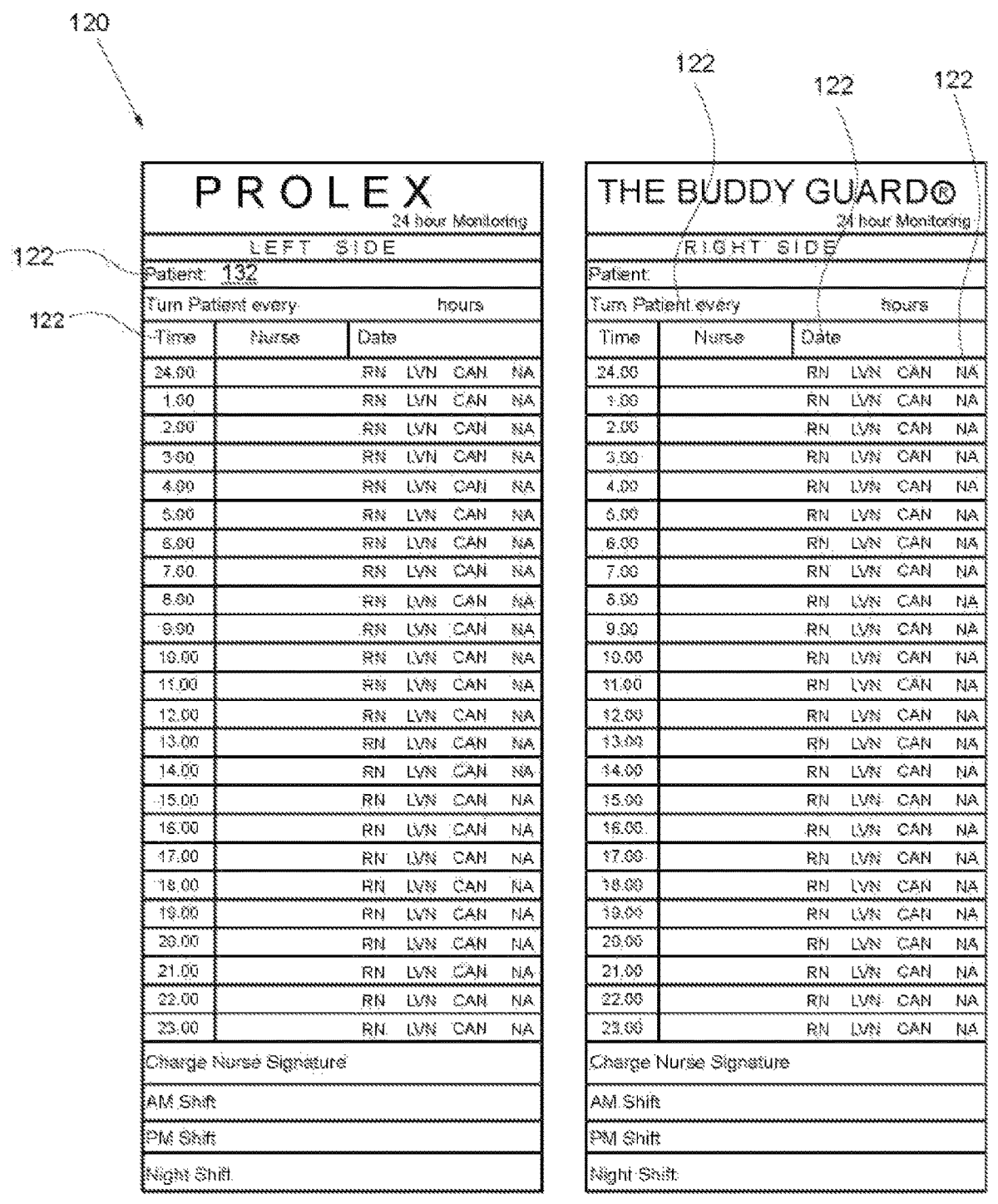

FIG. 3 is a top view of at least one label containing fields for marking information pertinent to the patient, in accordance with an embodiment of the present invention;

Like reference numerals refer to like parts throughout the various views of the drawings.

DETAILED DESCRIPTION OF THE INVENTION

Figure 1:
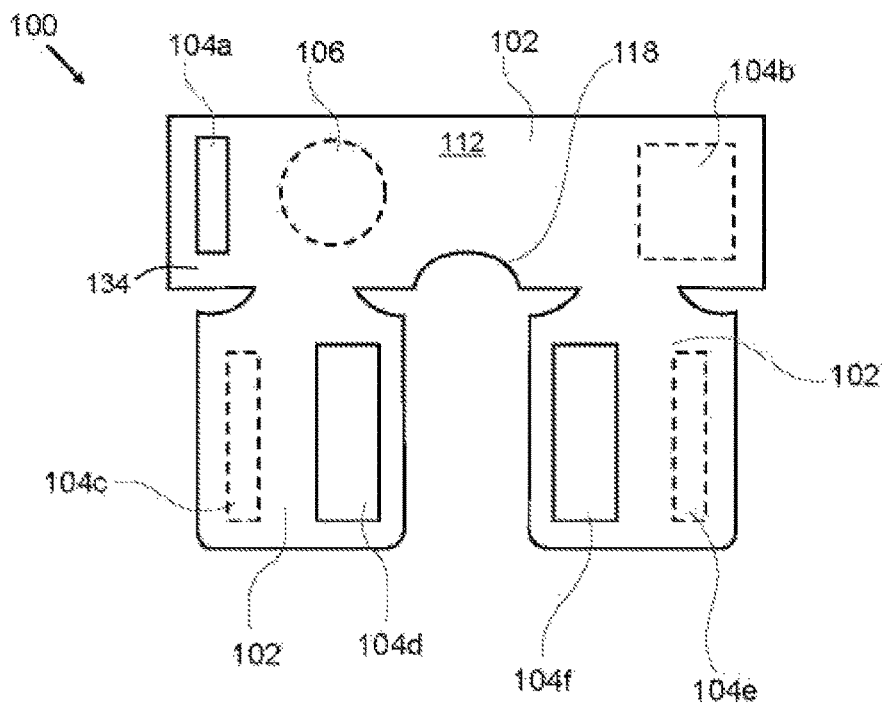
FIG. 1 is a plan view of an exemplary system for donning and labeling a body cast, showing a body cast according to the present invention while open, illustrating the location of detachable extra padding to protect the bony prominences of hip, buttock, and lower extremities, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

In one embodiment of the present invention presented in FIGS. 1-7, a system 100 and method for donning and labeling a body cast 130 enables a protective and pliable envelope to be donned and labeled directly on a patient. In this manner, the body of the patient is enclosed in a protective envelope for support and protection; and patient information is easily accessible directly from the body cast. The body cast 130 is pliable so as to be easily donned onto the patient with minimal skills and tools. The at least one label 120 that detachably attaches to the outer surface of the body cast. The label 120 may include pertinent patient personal and medical information about the patient, medical provider, and medical facility serving the patient.

As illustrated in FIG. 1, the system 100 is essentially a labeled protective enclosure with labels. The system may include a body cast 130 provides: 1) padded protection around the lower torso 400, legs 402a, 402b, the hip, the buttock, and the lower extremity pressure points for a bedridden patient; 2) unique nanomaterial fabrication; and easily accessible detachable labeling that indicates patient information. The labeled protective enclosure body cast 130 is comprised of multiple layers of nanomaterials and padding, that make up an enclosing support wrap 102. The support wrap 102 may be fabricated from a nonwoven cloth and comprises an inner surface 112 and an outer surface 124. The inner surface 112 engages the lower torso and legs, while the outer surface 124 is generally visible when the body cast 130 is donned.

In one possible embodiment, the body cast 130 is sectioned into an upper portion 114 that encloses generally the lower torso region of the body; and a pair of lower portions 116a-b that enclose, generally the legs. The upper and lower portions 114, 116a-b are adjacent and abut each other, or may integrate into each other.

In one embodiment, the body cast 130 is fabricated from a soft, pliable, nanomaterial that protects against moisture, odors, and bacteria. At least one label 120 provides a field that receives marking of information 122 pertinent to the patient. The label 120 detachably attaches to the lower portions 116a-b on the support wrap 102 to provide a caregiver easy access to patient information 122.

In other embodiments, the body cast 130 serves multiple purposes for a bedridden patient and the caregiver who is monitoring and providing medical care to the patient. The chief use is to protect the hip, buttock, and lower extremity pressure points from bruising. In addition to the padded composition of the support wrap 102, at least one auxiliary padding 106 detachably attaches to the support wrap 102 to further enhance the padding effect. The padding effect is especially effective after a patient has been bedridden for an excessive duration.

The body cast 130 is also unique in that it is substantially fabricated substantially from a nanomaterial that is water resistant, dirt free, odorless, anti-UV, and antibacterial. The naonmaterial is infused and crystalized with nanominerals 134 for optimal advantageous. The nanomaterial is efficacious for helping a bedridden patient be more protected against normal bedridden problems, such as urine, soil, skin irritation, and spilling drinks and food.

The system 100 also provides at least one label 120 that detachably attaches to the outer surface 124 of the support wrap 102. The label 120 that enables facilitated access to a caregiver for reading and marking information 122 and updates that are pertinent to the patient. The information may include the name of the bedridden patient, the time the bedridden patient was last examined, the date the patient was last examined, special instructions to and from a caregiver, information about the medical provider and the medical facility serving the patient.

In one exemplary embodiment of the system 100 for donning and labeling a body cast to provide cushioning for a patient's body from waist to knee and access patient information, a body cast 130 is provided to encase the lower torso 400 and legs 402a-b of the patient. The body cast 130 comprises a support wrap 102 and an inner lining 112. The support wrap 102 is defined by a nanomaterial, the cloth support wrap 102 comprising an upper portion 114 defined by a plurality of upper free ends.

The upper portion 114 is operable to at least partially enclose a lower torso 400 when the plurality of upper free ends overlap. The cloth support wrap 102 further comprises a pair of lower portions 116a-b defined by a plurality of lower free ends. The lower portion 116a-b is operable to enclose a leg when the plurality of lower free ends overlap. The body cast 130 further comprises an inner lining 112 that is defined by a soft pliable foam rubber material. The inner lining is enveloped by the cloth support wrap 102. In this manner, the inner lining helps cushion the lower torso 400 and the legs 402a-b.

The system 100 further comprises at least one auxiliary padding 106 that is detachably attachable to the body cast 130. The auxiliary padding helps provide cushioning for the lower torso and the legs. A plurality of fasteners 104a-f are placed at predetermined locations on the support wrap 102. The fasteners enable closure of the cloth support wrap 102 around the lower torso and the legs. The system 100 further comprises at least one label 120. The label 120 comprises a field for marking information 122. The label 120 is detachably attachable to the upper portion, or the pair of lower portions, or both of the support wrap 102.

Looking at FIG. 1, the system 100 provides a body cast 130 that easily wraps around the torso 400 and legs 402a-b of the patient from an opened, flat configuration. The body cast 130 is simply closed with adjustable hook and loop fastener latches, which facilitates proper fit and comfort. The body cast also is designed to provide an opening for urination or catheterization. For purposes of bathing or personal hygiene, the hook and loop fastener latches are released and the enclosure is opened to allow free access to the patient without discomfort.

The objects and advantages of such a flexible body cast are numerous. In one embodiment, the body cast 130 enables the relief and removal of pressure to the skin from bony prominences of the hip and buttock areas. In another embodiment, the body cast 130 allows for stimulation and circulation for bedridden persons unable to move frequently. In another embodiment, the body cast 130 allows the patient to keep the skin protected from abrasive materials such as starched sheets and mattress covers and the residual laundry chemicals left on the sheets. In another embodiment, the body cast 130 allows a caregiver to maintain a record of the patient attached directly onto the leg area for easy reading and marking. In another embodiment, the body cast 130 helps to protect a bedridden patient against normal bedridden problems, such as urine, soil, skin irritation, and spilling drinks and food.

Further objects and advantages are to provide that the protective enclosing device be easily and conveniently opened and closed with minimal discomfort to the patient, which can increase muscular, skin and vascular tone through unrestricted blood circulation. Among other advantages, the present invention eliminates the need for rubber rings or doughnuts that merely increase the pressure around bony prominences.

As shown in FIG. 1, the body cast has a support wrap 102 that forms an outer or foundation portion. The support wrap 102 may include a sturdy, flame-retardant, low-friction nanomaterial such as nylon to facilitate easier movement on a bed surface by reducing drag friction. Suitable low-friction nanomaterials may include, without limitation, Nylon, rayon and Dacron. These materials are also moisture-resistant and will retard the absorption of any body fluids from the patient. Additionally, the nanomaterial is also flame-retardant in accordance with both OSHA and local safety regulations. In one alternative embodiment, the nanomaterial comprises nanominerals infused and crystalized into the nanomaterial. In yet another aspect, the nanomaterial is water resistant, dirt free, odorless, anti-UV, and antibacterial.

In some embodiments, a plurality of fasteners 104a-f are attached to the support wrap 102 to facilitate opening and closing as well as allow for adjustment to body size and patient comfort. In one embodiment, the fasteners 104a-f include at least one hook and loop latches or fasteners.

At least one auxiliary padding 106 is also provided to be attached on the support wrap 102 at locations of the body where extra padding is needed to further cushion bony prominences of the patient. The auxiliary padding may be detachable through various means, including hook and loop fasteners, buttons, pins, and magnets.

Figure 2:
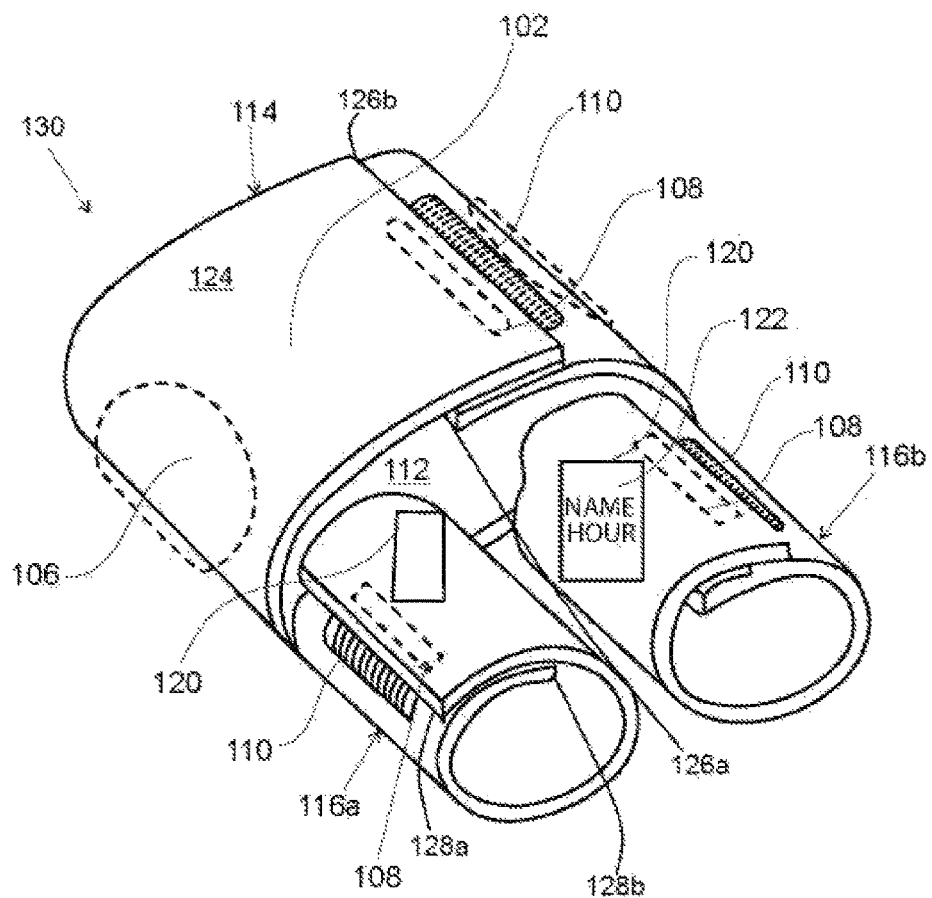
FIG. 2 is a perspective view showing the support wrap as it would appear when wrapped around a patient's body, cushioning bony prominences of the torso, hips and upper portions of the legs, in accordance with an embodiment of the present invention.

FIG. 2 illustrates a perspective view of the body cast 130. The support wrap 102 is closed around a patient's body. The fasteners 104a-f allow the device to be closed as firmly or as loosely as comfort dictates. In one embodiment, the fasteners include a hook and loop latch having a hook tape 108 and a loop tape 110. Loop tape 110 is made larger in width than tape 108 to permit adjustability and thereby fit the support wrap to the correct size for the patient. The dimensions of the present invention will vary with the size of the patient: small, medium, and large. The dimensions also accommodate variations in accordance with sex, age, and body measurements.

The outer support wrap 102 comprises an upper portion 114 defined by a plurality of upper free ends 126a, 126b. The upper portion 114 is sized and dimensioned to enclose the lower torso of the patient's body when the upper free ends 126a-b overlap each other. In one embodiment, the upper portion forms a cylindrical shape when enclosed around the lower torso.

In addition to the upper portion 114, the support wrap 102 further comprising a pair of lower portions 116a-b. The lower portions are defined by a plurality of lower free ends 128a, 128b. The lower portions 116a-b further sized and dimensioned to enclose each leg of the patient's body when the plurality of lower free ends 128a-b overlap each other. In one embodiment, the lower portions 116a-b may include two cylindrical shapes when enclosed around the legs.

Looking back at FIG. 2, at least one label 120 may detachably attach to the support wrap 102 of the pair of lower portions 116a-b. The label 120 provides a field 132 for marking information 122 pertinent to caring for the bedridden patient. The information 122 may include the name of the bedridden patient, the time the bedridden patient was last examined, and instructions from a caregiver. In one possible embodiment, illustrated in FIG. 3, the information 122 includes the name of the patient, the hours the patient was visited, the data the patient was visited, notations from a caregiver, and the position of the caregiver. Fields are allowed for enabling marking on the label 120. It is significant to note that the system 100 is unique in that the labels can be changed to accommodate different conditions of the lower torso and legs. For example, as the legs mend, the treatment or application of pressure on the legs may be reduced.

The outer support wrap 102 also serves as an envelope for an inner lining 112. The inner lining 112 is the layer that engages the patient. The inner lining 112 may be fabricated from a softer material such as a composite foam rubber. The inner lining 112 is soft and pliable, providing a cushioning effect to prevent hard contact between the patient's bony prominences and bed or chair surfaces, and to allow inflamed areas of the patient's body to breathe and benefit from the increase in blood circulation which is permitted to existing skin lesions or bed sores.

The manner of using the body cast 102 is simple and convenient for the attending health care provider or family member. The patient is placed on the opened device so that the lower body portion of the patient's torso is placed on the upper portion 114 of the support wrap. The patient is centered on upper portion 114 with the buttocks situated along the upper portion 114 and the legs overlying the lower portions 116a-b of the support wrap. The support wrap 102 is then closed and covers the body from waist area to the knees with the inner lining protecting and cushioning the hips bony prominences, buttocks, and upper parts of the legs and at the same time a crotch region 118 permits catherization and urination.

When the support wrap 102 is closed, the upper portion 114 and lower portions 116a-b are held in place on the patient's body by the fasteners 104a-f, such as hook and loop latches. The fasteners 104a-f are adjusted for body size and patient comfort. Opening the support wrap 102 is equally simple and easy by pulling the hook tape 108 and loop tape 110 apart to free the overlapping edges of the support. Because the low friction exterior material of the wrap 102 does not create drag friction with the bed surface, the support wrap can be easily slid out from under the patient if removal is desired.

The present invention thus protects and supports the body easily and conveniently, can be closed and reopened as often as needed as treatment or hygiene requires, and can be removed without discomfort to the individual. The invention thus relieves pressure on skin and subcutaneous tissue; prevents sensory loss, or absence of the patient's awareness of pain and pressure; permits the supply of nutrients to tissue cells, thus avoiding edema, by improved blood circulation which, in turn, aids the healing of existing ulcers or bed sores; and facilitates increased activity by the patient because the device reduces or eliminates the discomfort of motion, allowing activity to thereby increase muscular, skin, and vascular tone.

The present invention also provides at least one detachable label 120 that is easy to access without having to turn over a patient. The label helps a care provider maintain better records on the patient without disturbing the patient to turn over. Also, the label 120 is less likely to get lost since it adheres directly to the support wrap 102. The present invention is also fabricated from a nanomaterial that creates many advantages that overcome the problems associated with being bedridden.

Figure 4:
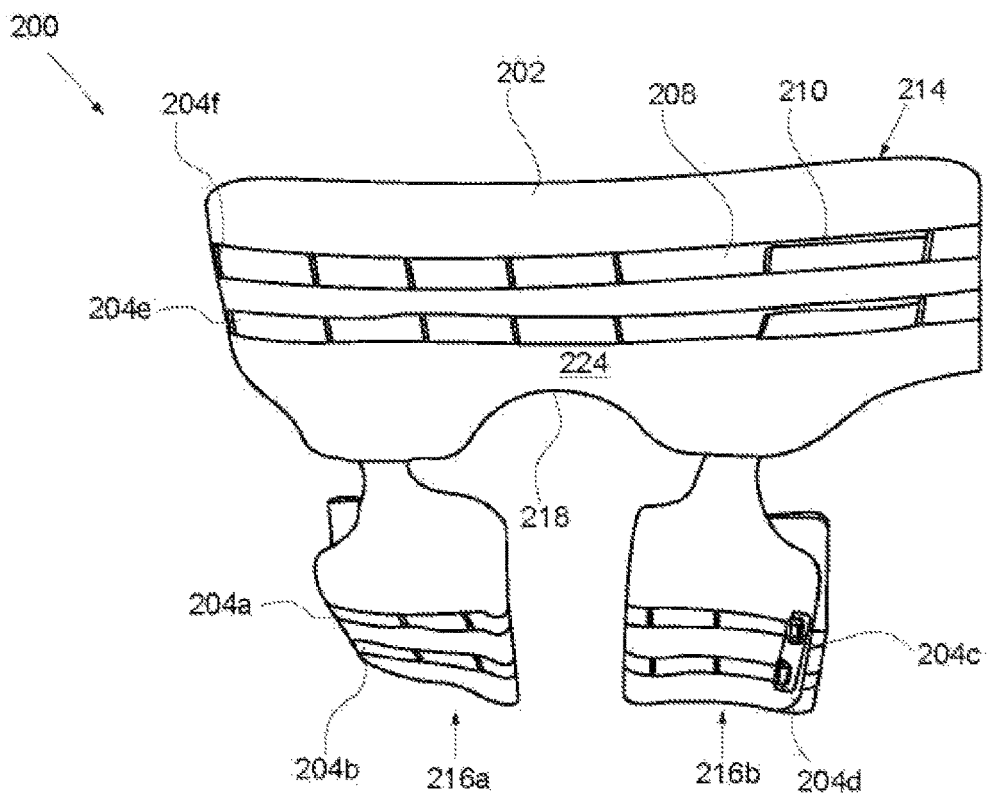
FIG. 4 is a top angle perspective view of an inner side of an alternative labeled protective enclosure body cast having a larger crotch region, in accordance with an embodiment of the present invention.

FIG. 4 is a top angle perspective view of an inner side of an alternative labeled protective enclosure body cast 200 having a larger crotch region 218. In this alternative version, the upper portion 214 of the support wrap still utilizes a crotch region configured to permit catherization and urination. However, here, the crotch region 218 is larger to allow more field for the genitals and working around the genitals. The lower portions 216a, 216b remain substantially the same. Also, the hook tape 208, loop tape 210, and fasteners 204a-f extend lengthwise across the support wrap 202.

Figure 5:
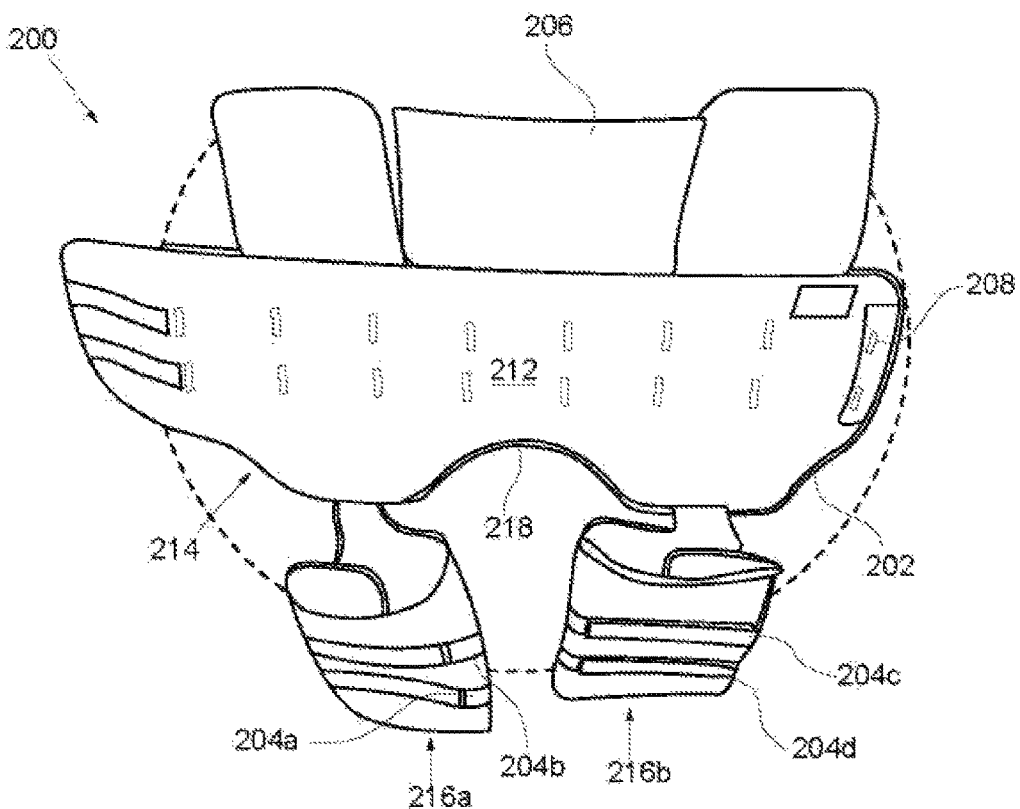
FIG. 5 is a top angle perspective view of an outer side of an alternative labeled protective enclosure body cast having a larger crotch region, in accordance with an embodiment of the present invention.

Turning now to FIG. 5, a top angle perspective view of an outer surface 124 of the support wrap 102 is illustrated. Here it is shown that the auxiliary pad 206 extends from the upper portion 214. The auxiliary pad 206 may also be integrated into the body cast 130 or the support wrap 102 of the body cast. In any case, the auxiliary pad 206 provides additional cushioning for the lower torso 400 and legs 402a-b, so as to minimize bruising while handling the patient.

Figure 6A:
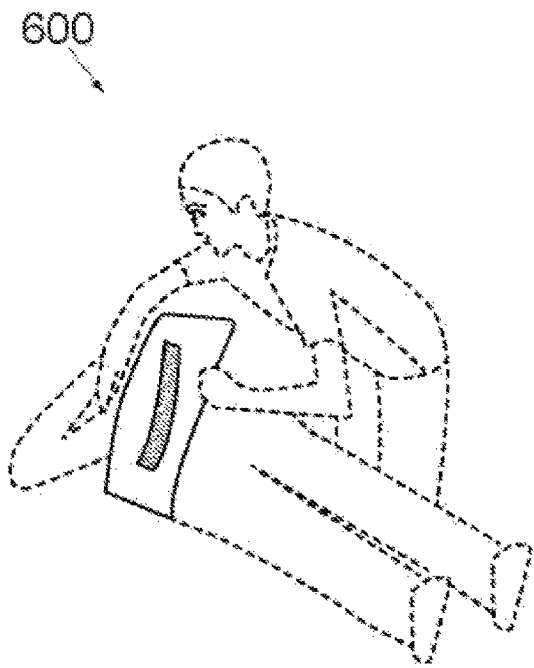
FIGS. 6A-6R illustrate perspective illustrations showing sequential steps for donning the labeled protective enclosure body cast, and manipulating the patient once the body cast is donned, in accordance with an embodiment of the present invention.
Figure 6B:
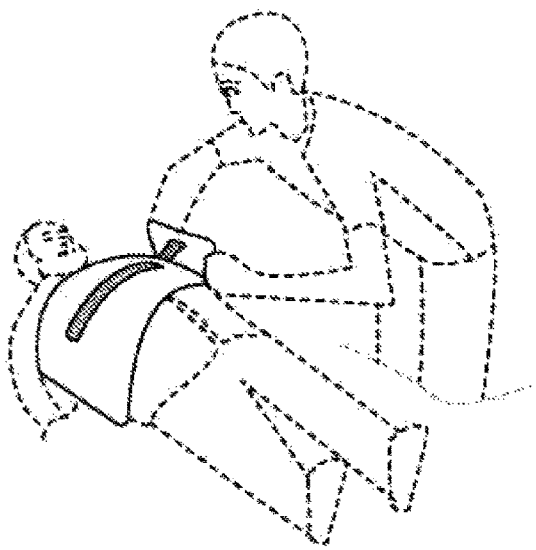
Figure 6C:
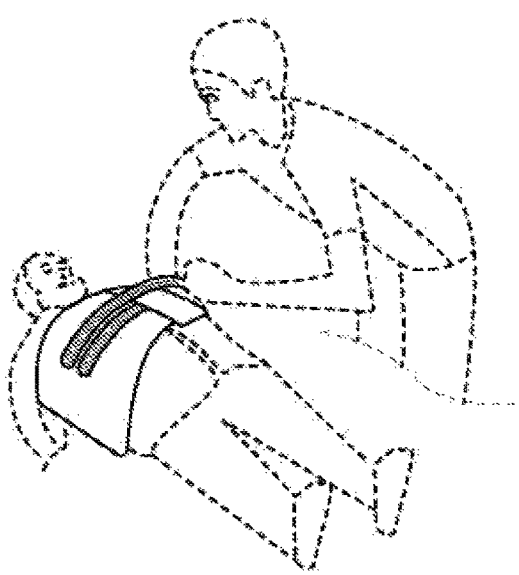
Figure 6D:
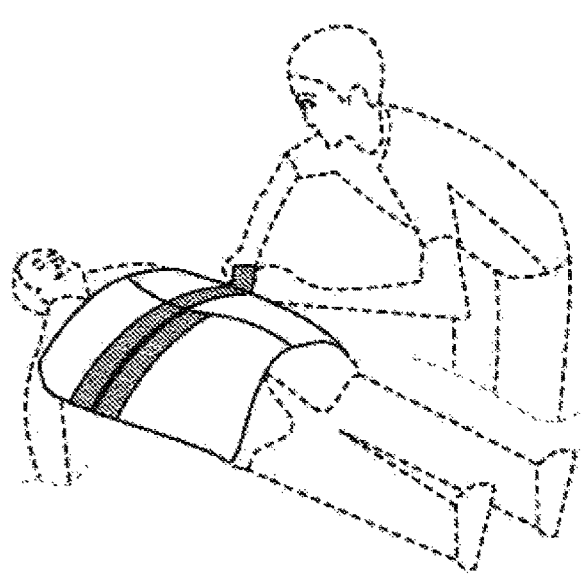
Figures 6E, 6F:
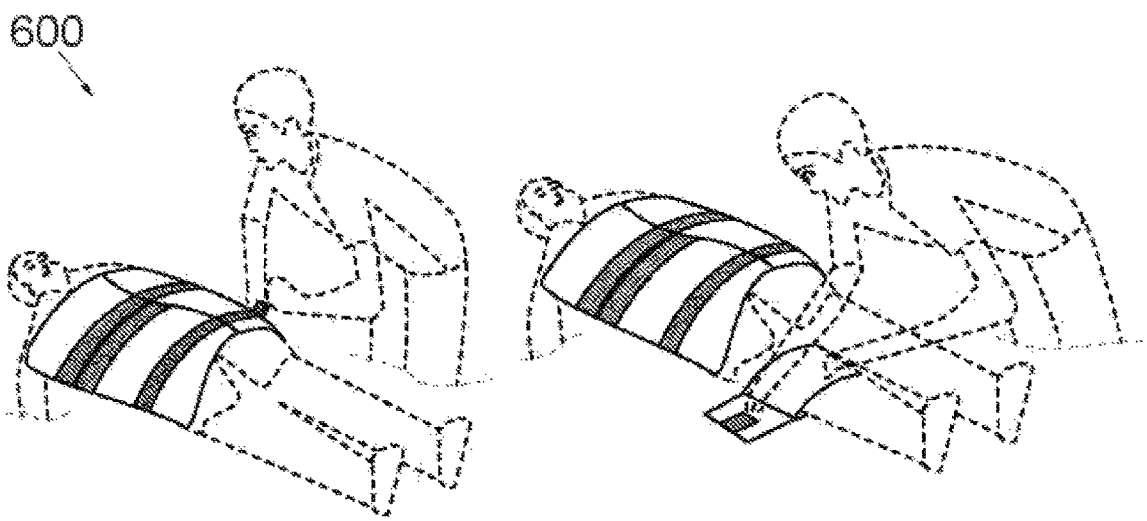
Figures 6G, 6H:
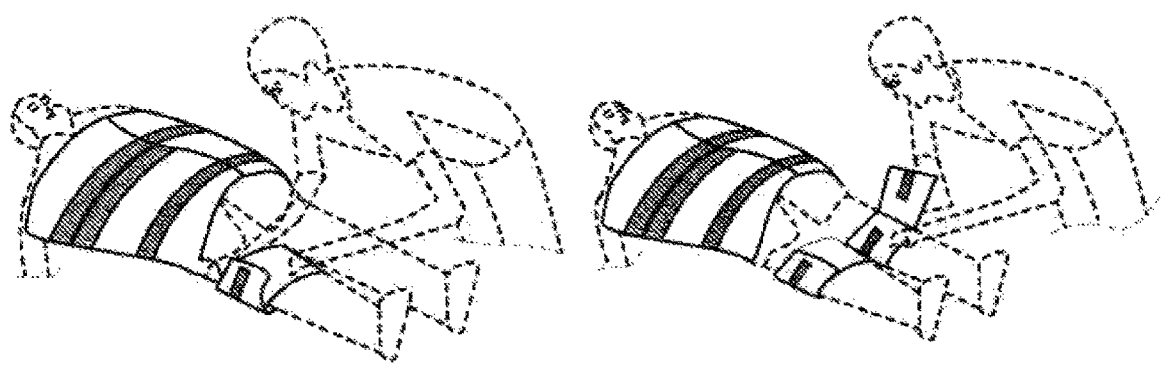
Figure 6I:
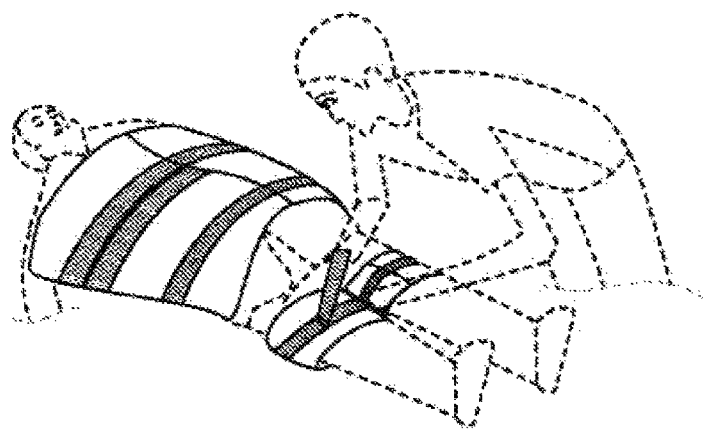
Figure 6J:
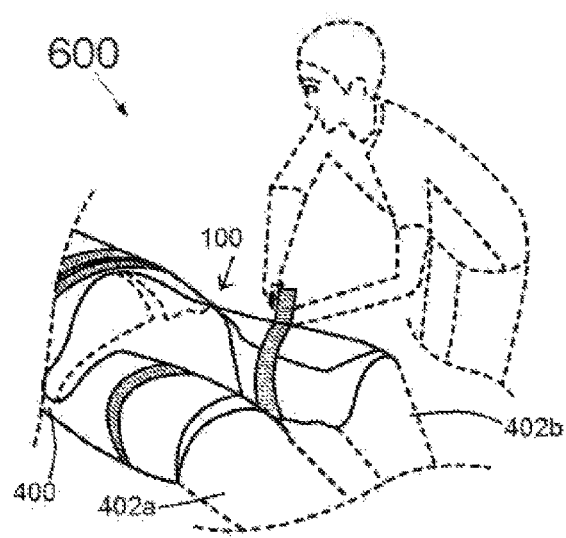
Figure 6K:
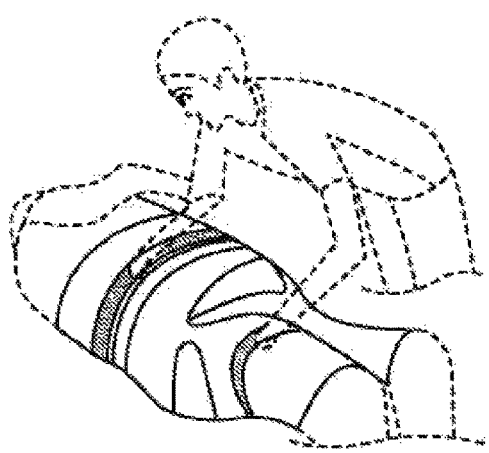
Figure 6L:
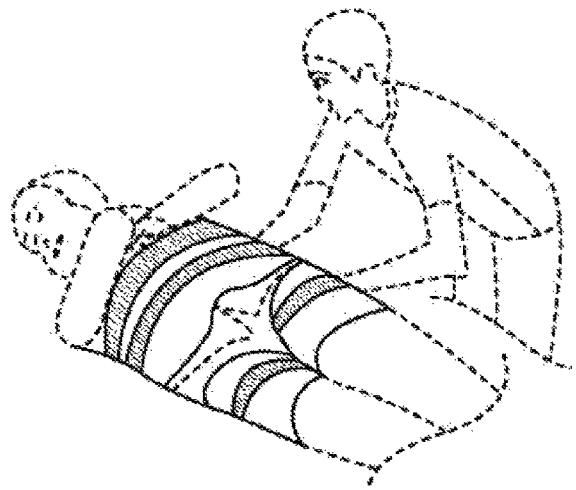
Figure 6M:
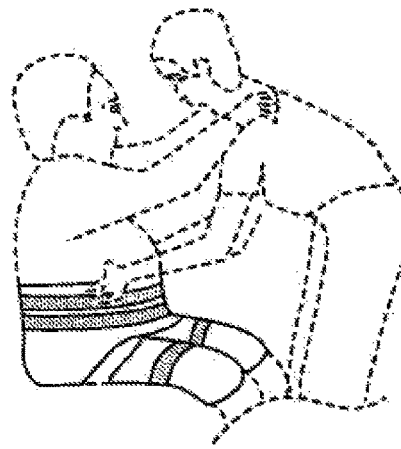
Figure 6N:
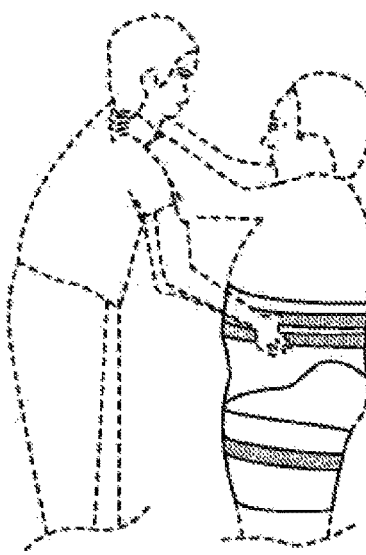
Figure 6O:
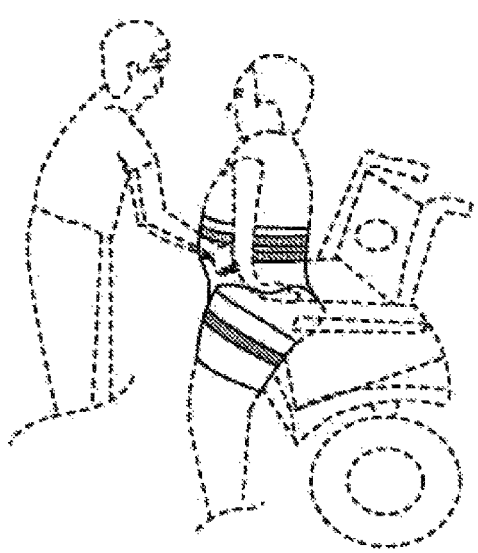
Figure 6P:
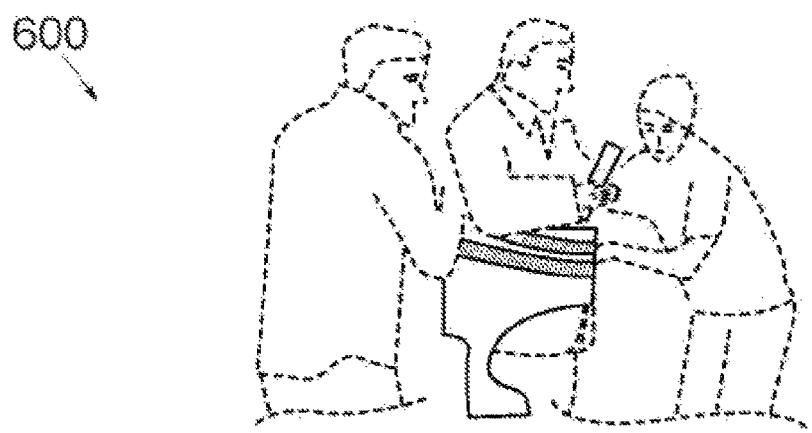
Figure 6Q:
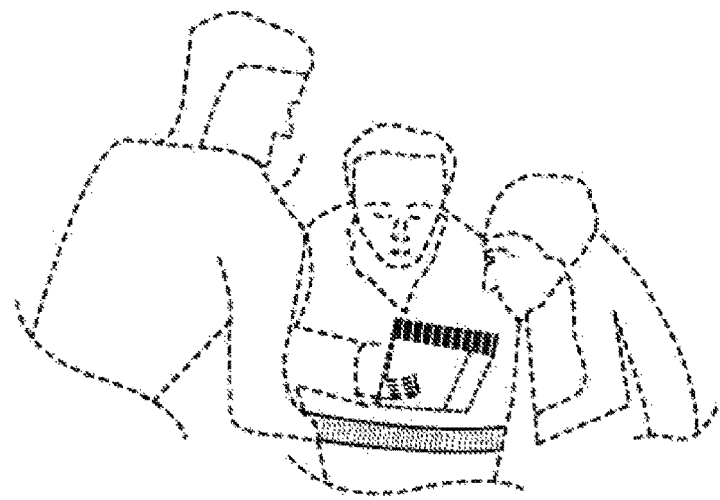
Figure 6R:
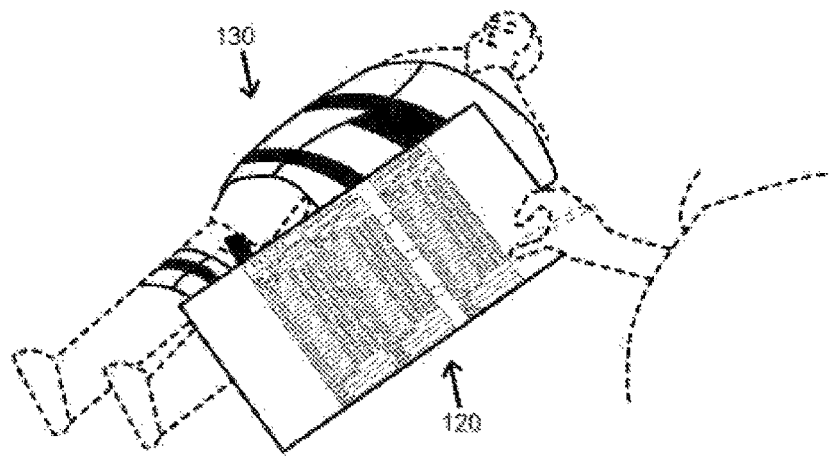

FIGS. 6A-6R illustrate perspective illustrations showing sequential steps of a method 600 for donning the labeled protective enclosure body cast 130 on a patient and manipulating the patient once the body cast is donned. FIG. 6A illustrates laying the body cast 130 on a bed under the patient and folding one end of the support wrap 102 over to a second end until the fasteners align. FIG. 6B shows folding the opposite side of the support wrap 102 until the hook tape 108 and loop tape 110 align. FIG. 6C shows bringing the hook tape 108 across the patient's chest and feeding it through the attached loop tape 110.

FIG. 6D illustrates pulling the hook tape 108 tight and pulling it back to seal with the loop tape 110. FIG. 6E shows performing the same hook tape 108 tightening with a second set of hook tape and loop tape. FIG. 6F shows folding over a flap from one end of the lower portion 116a over the upper right thigh and above the right knee. FIG. 6G shows pulling the opposite flap to join with the first flap at the lower portion 116a.

FIG. 6H shows folding over a flap from one end of the lower portion 116b over the upper left thigh and above the left knee. FIG. 6I shows pulling the opposite flap to join with the first flap at the lower portion 116b. FIG. 6J illustrates feeding the loop tape 108 from the other end of the lower portion 116b through the loop and pulling securely, fastening it back on the loop tape 110. This junction between hook tape 108 and loop tape 110 creates a handle on each side of the patient. The handle is efficacious for manipulating the patient.

FIG. 6K illustrates turning the patient to the right by placing the fingers in the handles created by the hook tape 108 and loop tape 110, and gently pulling. FIG. 6L illustrates turning the patient to the left by placing the fingers in the handles created by the hook tape 108 and loop tape 110, and gently pulling. FIG. 6M shows assisting a patient to stand by gripping the handles on the sides and lifting. FIG. 6N illustrates slowly assisting the patient in making necessary movements to achieve a seated position.

FIG. 6O shows lowering the patient into a seat while still gripping the handles. FIG. 6P illustrates how two caregivers can support the patient, with each caregiver grabbing a handle from the respective side of the patient. FIG. 6Q shows how the body cast 130 can be constantly worn and used for facilitating movement to the bathroom. FIG. 6R illustrates the label 120 as a 24-hour monitoring sheet on each lower portion 116a, 116b so that it can be viewed whether the patient is turned to the left or the right.

Figure 7:
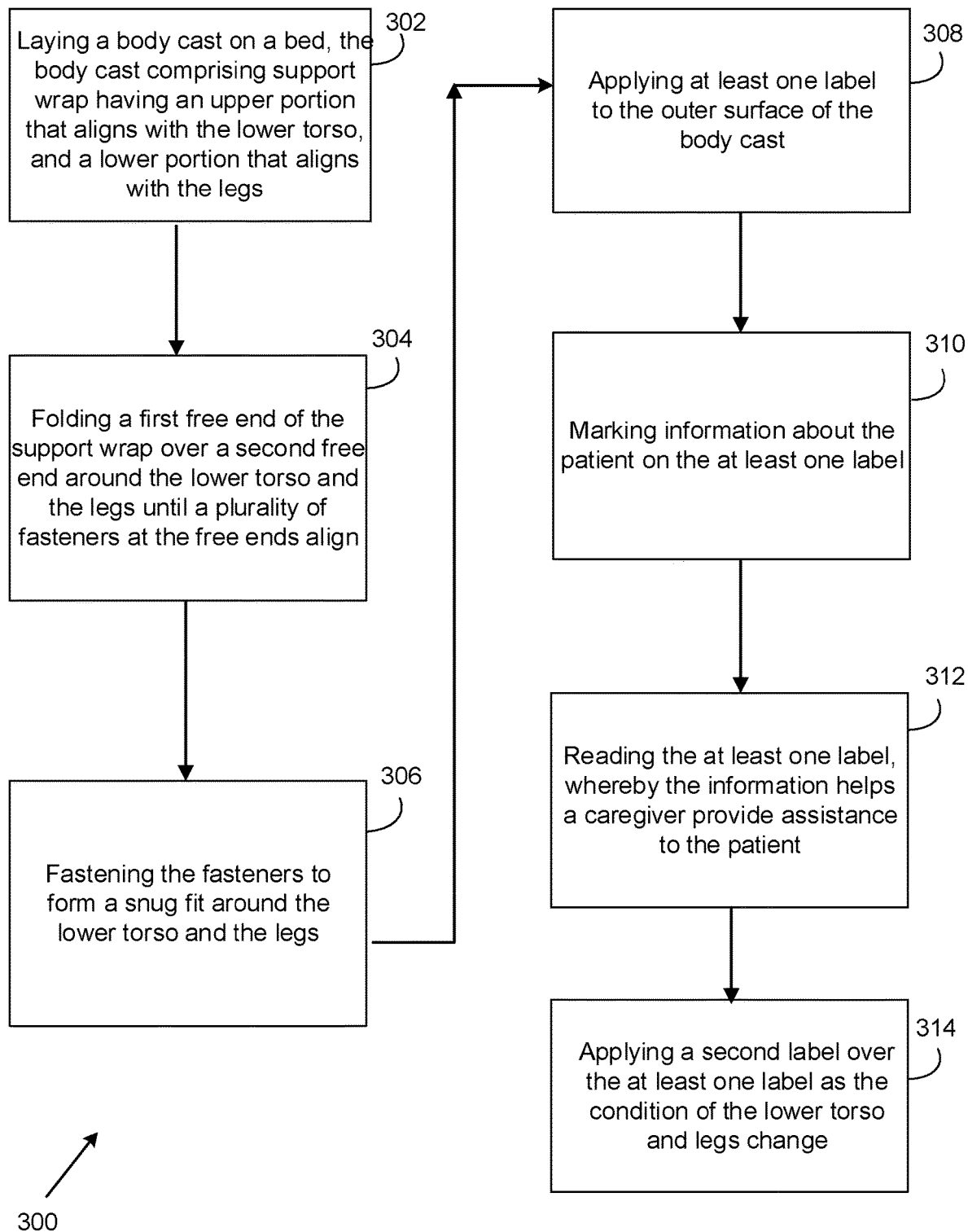
FIG. 7 illustrates a flowchart for an exemplary method for donning and labeling a body cast, in accordance with an embodiment of the present invention.

Yet another means to don and label the body cast is exemplified in FIG. 7, which illustrates a flowchart of a method 300 for donning and labeling a body cast. In one embodiment, the method 300 includes an initial Step 302 of laying a body cast on a bed, the body cast comprising support wrap having an upper portion that aligns with the lower torso, and a lower portion that aligns with the legs.

The method 300 may further comprise a Step 304 of folding a first free end of the support wrap over a second free end around the lower torso and the legs until a plurality of fasteners at the free ends align. The support wrap 102 is pliable, and may be fabricated from rubber, so as to enable facilitated pulling in this manner. A Step 306 includes fastening the fasteners to form a snug fit around the lower torso and the legs.

In some embodiments, a Step 308 comprises applying at least one label to the outer surface of the body cast. The label may include an adhesive that allows for interchanging labels as the condition of the lower torso and legs changes. A Step 310 includes marking information about the patient on the at least one label 120. The label provides fields 132 that enable marking of pertinent information. In some embodiments, a Step 312 may include reading the at least one label, whereby the information helps a caregiver provide assistance to the patient.

A final Step 314 includes applying a second label over the at least one label as the condition of the lower torso and legs change. The method 300 is unique in that multiple labels can be changed to accommodate different conditions of the lower torso and legs. For example, as the legs mend, the treatment or application of pressure on the legs may be reduced.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A support wrap comprising:
   an upper portion, wherein
   the upper portion of said the support wrap having a first side extending along a first direction by a first length,
   the upper portion of said the support wrap having a second side extending along a second direction by a second length,
   the upper portion of said the support wrap having a third side extending along a third direction by a third length,
   the first direction is in a different direction than the second direction,
   the first direction is in a different direction than the third direction,
   the first length being greater than the second length,
   the first length being greater than the third length,
   the upper portion including a first upper fastening member,
   the upper portion including a second upper fastening member,
   said first upper fastening member capable of fastening said second side to said third side, said second upper fastening member capable of fastening said second side to said third side, and the upper portion of said the support wrap having a fourth side extending along a fourth direction by a fourth length;

a first lower portion having at least a first lower length wherein the first lower portion length extends along the first direction; and a second lower portion having at least a second lower length wherein the second lower portion length extends along the first direction, wherein the first lower portion extending from the fourth side and extending away from upper portion, the second lower portion extending from the fourth side and extending away from upper portion, said first upper fastening member includes a first upper hook and loop mechanism extending along the first direction, said second upper fastening member includes a second upper hook and loop mechanism extending along, the first direction, said first upper hook and loop mechanism creates a first upper handle in a case that the first upper hook and loop mechanism is fastened, said second upper hook and loop mechanism creates a second upper handle in a case that the second upper hook and loop mechanism is fastened, the first lower portion includes a first lower fastening member and a first lower hook and loop mechanism, the second lower portion includes a second lower fastening member and a second lower hook and loop mechanism, the first lower hook and loop mechanism extending along the first direction wherein the first lower hook and loop mechanism having a first lower hook and loop mechanism length extending along the first direction, the second lower hook and loop mechanism extending along the first direction wherein the second lower hook and loop mechanism having a second lower hook and loop mechanism length extending along the first direction, the first lower hook and loop mechanism length is greater than the first lower portion length, the second lower hook and loop mechanism length is greater than the second lower portion length, said first lower hook and loop mechanism creates a first lower handle in a case that the first lower hook and loop mechanism is fastened, and said second lower hook and loop mechanism creates a second lower handle in a case that the second lower hook and loop mechanism is fastened.

2. The support wrap according to claim 1, wherein the area of said first side is different from the area of said second side.

3. The support wrap according to claim 1, further comprising:

a first transition portion; and a second transition portion, wherein the first lower portion extending from the fourth side via the first transition portion, the second lower portion extending from the fourth side via the second transition portion, the first transition portion extending from the fourth side and extending away from upper portion, the first transition portion having a first transition width, the second transition portion extending from the fourth side and extending away from upper portion, the second transition portion having a second transition width, the first lower portion having a first lower width, the second lower portion having a second lower width, the first lower width and the second lower width are greater than the first transition width and the second transition width, and the first length and the fourth length are greater than the first transition width, the second transition width, the first lower width and the second lower width.

4. The support wrap according to claim 1, wherein at least one auxiliary padding detachably attachable to the support wrap.

5. The support wrap according to claim 1, wherein a plurality of auxiliary padding detachably attachable to the support wrap.

6. The support wrap according to claim 1, wherein at least one auxiliary padding detachably attachable to the upper portion.

7. The support wrap according to claim 1, wherein a plurality of auxiliary padding detachably attachable to the upper portion.

8. The support wrap according to claim 1, wherein the first upper hook and loop mechanism length is greater than the first length, and the second upper hook and loop mechanism length is greater than the first length.

9. A support wrap comprising:

an upper portion, wherein the upper portion of said the support wrap having a first side extending along a first direction by a first length, the upper portion of said the support wrap having a second side extending along a second direction by a second length, the upper portion of said the support wrap having a third side extending along a third direction by a third length, the first direction is in a different direction than the second direction, the first direction is in a different direction than the third direction, the first length being greater than the second length, the first length being greater than the third length, the upper portion having an inner surface and an outer surface, the outer surface including a first upper fastening member, the upper portion including a second upper fastening member, said first upper fastening member capable of fastening said second side to said third side, said second upper fastening member capable of fastening said second side to said third side, and the upper portion of said the support wrap having a fourth side extending along a fourth direction by a fourth length;

a first lower portion;

a second lower portion;

a first transition portion;

a second transition portion;

the first transition portion extending from the fourth side and extending away from upper portion, the first transition portion having a first transition width, the second transition portion extending from the fourth side and extending away from upper portion, the second transition portion having a second transition width, the first lower portion extending from the first transition portion and extending away from upper portion, the first lower portion having a first lower width, the second lower portion extending from the first transition portion and extending away from upper portion, the second lower portion having a second lower width, the first lower width and the second lower width are greater than the first transition width and the second transition width, the first length and the fourth length are greater than the first transition width, the second transition width, the first lower width and the second lower width, said first upper fastening member includes a first upper hook and loop mechanism extending along the first direction, said second upper fastening member includes a second upper hook and loop mechanism extending along the first direction, said first upper hook and loop mechanism creates a first upper handle in a case that the first upper hook and loop mechanism is fastened, said second upper hook and loop mechanism creates a second upper handle in a case that the second upper hook and loop mechanism is fastened, the first lower portion includes a first lower fastening member and a first lower hook and loop mechanism, the second lower portion includes a second lower fastening member and a second lower hook and loop mechanism the first lower hook and loop mechanism extending along the first direction wherein the first lower hook and loop mechanism having a first lower hook and loop mechanism length extending along the first direction, the second lower hook and loop mechanism extending along the first direction wherein the second lower hook and loop mechanism having a second lower hook and loop mechanism length extending along the first direction, the first lower hook and loop mechanism length is greater than the first lower portion length, the second lower hook and loop mechanism length is greater than the second lower portion length, said first lower hook and loop mechanism creates a first lower handle in a case that the first lower hook and loop mechanism is fastened, and said second lower hook and loop mechanism creates a second lower handle in a case that the second lower hook and loop mechanism is fastened.

10. The support wrap according to claim 9, wherein
the area of said first side is different from the area of said second side.

11. The support wrap according to claim 9, wherein
at least one auxiliary padding detachably attachable to the support wrap.

12. The support wrap according to claim 9, wherein
a plurality of auxiliary padding detachably attachable to the support wrap.

13. The support wrap according to claim 9, wherein
at least one auxiliary padding detachably attachable to the upper portion.

14. The support wrap according to claim 9, wherein
a plurality of auxiliary padding detachably attachable to the upper portion.

15. The support wrap according to claim 9, wherein
the first upper hook and loop mechanism length is greater than the first length, and the second upper hook and loop mechanism length is greater than the first length.

* * * * *